(12) United States Patent  
Licha (10) Patent No.: US 8,590,193 B2  
(45) Date of Patent: Nov. 26, 2013

(54) LABEL, USE OF A RAISED STRUCTURAL FEATURE, INJECTION DEVICE, AND METHOD FOR PRODUCING A LABEL

(75) Inventor: Robert Licha, Ottobrunn (DE)

(73) Assignee: Schreiner Group GmbH & Co. KG, Oberschleissheim (DE)

( * ) Notice: Subject to any disclaimer, the term of this patent is extended or adjusted under 35 U.S.C. 154(b) by 404 days.

(21) Appl. No.: 12/804,611

(22) Filed: Jul. 26, 2010

(65) Prior Publication Data

US 2011/0028907 A1  Feb. 3, 2011

(30) Foreign Application Priority Data

Jul. 27, 2009  (DE) .......................... 10 2009 034 823

(51) Int. Cl.  
  *G09F 3/10*  (2006.01)

(52) U.S. Cl.  
  USPC ............................................ 40/638; 604/189

(58) Field of Classification Search  
  USPC .................................................... 40/306, 310  
  See application file for complete search history.

(56) References Cited

U.S. PATENT DOCUMENTS

| 1,032,610 A * | 7/1912 | Kern ........................... 250/462.1 |
| 5,857,275 A * | 1/1999 | Deal ................................ 40/310 |
| 6,951,353 B2 * | 10/2005 | Kozlowski et al. .............. 283/81 |
| 2004/0128877 A1 * | 7/2004 | Luedde ........................... 40/306 |
| 2004/0187370 A1 * | 9/2004 | Buzby ............................. 40/324 |
| 2004/0243054 A1 * | 12/2004 | Kraushaar ....................... 604/80 |
| 2006/0144942 A1 * | 7/2006 | Evans et al. .................... 235/435 |
| 2008/0262443 A1 | 10/2008 | Hommann |
| 2008/0308442 A1 * | 12/2008 | Spigelman et al. ........ 206/459.1 |
| 2009/0037221 A1 * | 2/2009 | Litherland et al. ................ 705/3 |

FOREIGN PATENT DOCUMENTS

| DE | 70 21 690 | 9/1970 |
| DE | 10 2005 052 460 | 5/2007 |
| DE | 10 2006 048 209 | 4/2008 |
| EP | 1 477 196 | 11/2004 |
| EP | 1 566 786 | 8/2005 |
| WO | WO 98/19289 | 5/1998 |

* cited by examiner

*Primary Examiner* — Joanne Silbermann  
*Assistant Examiner* — Kristina Junge  
(74) *Attorney, Agent, or Firm* — Collard & Roe, P.C.

(57) ABSTRACT

A label with a raised structural feature is for an injection device and includes a flexible support layer which, on one face, is provided at least partially with one or more of the raised structural element. The raised structural element is designed in such a way that, when the label is applied to a container of the injection device, the raised structural element is directed away from the container, and the raised structural element is able to establish a form-fit connection with another structural element, for example another structural element of the injection device. The label is formed by a method including steps of providing the flexible support layer and applying at least one raised structural element onto the flexible support layer.

40 Claims, 4 Drawing Sheets

LABEL, USE OF A RAISED STRUCTURAL FEATURE, INJECTION DEVICE, AND METHOD FOR PRODUCING A LABEL

CROSS REFERENCE TO RELATED APPLICATIONS

Applicant claims priority under 35 U.S.C. §119 of German Application No. 10 2009 034 823.9 filed Jul. 27, 2009.

BACKGROUND OF THE INVENTION

1. Field of the Invention

The invention relates to a label, to the use of a raised structural feature, to an injection device, and to a method for producing a label.

2. The Prior Art

Labels are often used to label medical containers, for example medicament ampoules for injection pens. Previously known labels have been used merely to identify the active substance contained in the medical container. The medical container is secured in the injection pen. The medicament ampoules normally have smooth side walls that are made of glass and that offer little if any possibility of securing the ampoule, and it is therefore sometimes difficult to secure medical containers in a medical device, for example an injection pen.

There is therefore a need to provide other possible ways of securing the containers.

SUMMARY OF THE INVENTION

This object is achieved, in a first aspect of the invention, by a label for labelling a container, comprising a flexible support layer which, on one face, is provided at least partially with at least one raised structural element, wherein the structural element is designed in such a way that, when the label is applied to the container, the structural element is directed away from the container, and wherein the structural element is able to establish a form-fit connection with another structural element.

By means of the label, it is possible, when applying the label to a container, to form a holding element for the container with the label, such that even containers that have no other possibilities of being held can be mounted in a housing, for example, or some other securing structure. The raised structural element can represent the sole holding possibility or an additional holding possibility. All in all, a label is obtained having the additional function of forming a holding element, such that several functions are integrated in one label in an inexpensive and simple manner, but without significantly complicating the process of producing the label.

According to another embodiment of the label, the structural element has a height that is greater than four times the support layer and preferably greater than twenty times the support layer. The structural element can, for example, have a height that is greater than 0.4 mm and that is preferably between 0.4 mm and 2.0 mm. When the label with the structural element is applied to a container, for example to a medicament ampoule, and the container is pushed into another container, for example the hollow body of a syringe, which likewise has further structural elements, it is ensured that the structural element of the label forms a stable abutment with the further structural element and thus establishes a form-fit connection. The structural element can be applied to the support layer via a face that is delimited by sides of the structural element. In this embodiment, the structural element can have a height that is at least twice as great as the shorter of the sides of the face.

In another embodiment, a multiplicity of structural elements are applied to the face of the support layer, and, when the label is applied to the container, this results in a multiplicity of holding elements directed away from the container. The holding elements can be designed, for example, as projections. This can further increase the holding ability of the label, which is particularly desirable if, when the label is applied to the container, the latter is exposed to considerable forces.

According to another embodiment, each of the structural elements of the multiplicity of structural elements has a side face. The structural elements are arranged on the support layer in such a way that the respective side face of the structural elements is arranged in one plane. When the label with the structural elements is applied to a body, for example a cylindrical container, the respective side faces of the structural elements form an abutment surface that lies in one plane. A further body that likewise has structural elements can be arranged in such a way that the further structural elements bear on the structural elements of the label in the plane in which the side faces are contained. A form-fit connection is thus established between the body to which the label is applied and the body on which the further structural elements are arranged.

The structural element can be bonded to the support layer by means of an adhesive layer, for example. The adhesive layer can be a layer that sets under the action of heat or radiation.

In another embodiment, the structural element is applied as a plastic web to the support layer. Plastic webs represent a simple and inexpensive way of forming raised structural elements, and this approach also permits integration into existing manufacturing installations for label production.

In another embodiment, the plastic web is adhesively bonded to the support layer. The adhesive bonding provides an inexpensive and simple connection between plastic web and support layer, which can likewise be integrated into existing manufacturing installations for label production.

According to another embodiment, the structural element is applied as a structured colour layer to the support layer. The structured colour layer can, for example, be printed onto the support layer by means of a paint. Printing is a standard step in label production, and therefore the process complexity is kept to a minimum and an inexpensive and simple possibility of label production is afforded.

In another embodiment, the paint corresponds to a printing ink for Braille. After they have been printed and have set, printing inks for Braille form structural elements that protrude distinctly from their background, thus affording an inexpensive and simple way of forming raised structural elements.

According to another embodiment, the structural element is applied as a structured film layer to the support layer. Application of film layers likewise represents a standard step in label production, and therefore the process complexity is kept to a minimum and an inexpensive and simple possibility of label production is afforded.

In another embodiment, the structured film layer is affixed to the support layer. The adhesive bonding provides an inexpensive and simple connection between film layer and support layer, which can likewise be integrated into existing manufacturing installations for label production.

In another embodiment, the flexible support layer additionally comprises symbols that represent information about the contents of the container, directions for use, or instructions from the manufacturer. In another embodiment, the symbols are printed onto the flexible support layer. Printing is a standard step in label production, and therefore the process complexity is kept to a minimum and an inexpensive and simple possibility of label production is afforded.

In another embodiment, the label can be secured to the container by means of an adhesive layer applied to another face lying opposite the face of the support layer.

In another embodiment, when the label is applied to the container, the raised structural element is suitable as an abutment for securing the container in a housing.

In another embodiment, several structural elements are applied parallel to one another on the support layer. In another embodiment, the parallel structural elements each have a starting point, and these starting points are arranged along a line.

According to another embodiment, the container is cylindrical, and the structural element is arranged along an axial direction of the container.

In another embodiment, the structural element forms a thread when the label is applied to the container.

In another embodiment, when the label is applied to the container, gaps in the structural element form the thread.

In another embodiment, an outer dimension of the label corresponds to an outer circumference of the container.

According to another embodiment, the multiplicity of structural elements are formed by a multiplicity of ball-shaped elements, wherein the ball-shaped elements are arranged on the face of the support layer in such a way that, when the label is applied to the container, the ball-shaped elements form the thread.

According to another aspect, at least one raised structural element on a label can be used, wherein the label is arranged on an outer face of a cylindrical container in such a way that the structural element is directed away from the outer face of the container and is able to establish a form-fit connection with another structural element. The structural element can be used on the label in such a way that the structural element performs a holding function in the form of an abutment or thread for the cylindrical container in a housing.

The object is achieved, in a further aspect of the invention, by a medical injection device, comprising:

a label with a flexible support layer which, on one face, is provided at least partially with at least one raised structural element, a cylindrical container which receives a medical product and which is provided with the label, wherein the label is arranged on the container via a face lying opposite the face and the structural element forms a projection directed away from the container, and a housing in which the container is arranged, wherein the structural element is able to establish a form-fit connection with another structural element.

According to another embodiment, the structural element performs a holding function in the form of an abutment or thread for the cylindrical container in the housing.

According to another embodiment, the structural element has a height that is greater than four times the support layer. For example, the structural element can have a height that is greater than 0.4 mm and that is preferably between 0.4 mm and 2 mm. The structural element can be applied to the support layer via a face that is delimited by sides of the structural element. In this embodiment, the structural element has a height that is at least twice as great as the shorter of the sides of the face.

According to another embodiment, a multiplicity of structural elements are applied to the face of the support layer, and, when the label is applied to the container, this results in a multiplicity of holding elements directed away from the container.

According to another embodiment of the medical injection device, the structural element is bonded to the support layer by means of an adhesive layer. The cylindrical container can be a medicament ampoule or a medicament cartridge, for example. According to another embodiment, the housing can be part of an injection pen or of a syringe. The container, at a distal end, can have a needle which is surrounded by a needle guard device.

A method for producing a label is set out below, said method comprising the following steps:

providing a flexible support layer, and applying at least one raised structural element to one face of the support layer, wherein the structural element is designed in such a way that, when the label is applied to the container, the structural element is directed away from the container, and wherein the structural element is able to establish a form-fit connection with another structural element.

According to the method, provision is further made that the structural element is applied to the support layer with a height that is greater than four times the support layer. The structural element can, for example, be applied to the support layer with a height that is greater than 0.4 mm and that is preferably between 0.4 mm and 2 mm. According to a development of the method, the structural element can be applied to the support layer via a face that is delimited by sides of the structural element. The structural element can be applied to the support layer with a height that is at least twice as great as the shorter of the sides of the face. The structural element can, for example, be bonded to the support layer by means of an adhesive layer.

Further advantages and features of the invention will become clear from the following description and from the figures in the drawings.

The invention is explained in greater detail below on the basis of illustrative embodiments and with reference to the drawings. Elements, areas and structures having the same function or action are provided with the same reference signs. Where elements, areas or structures correspond in terms of their function, the description thereof will not be repeated in each illustrative embodiment.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings.

DETAILED DESCRIPTION OF PREFERRED EMBODIMENTS

Figure 1:
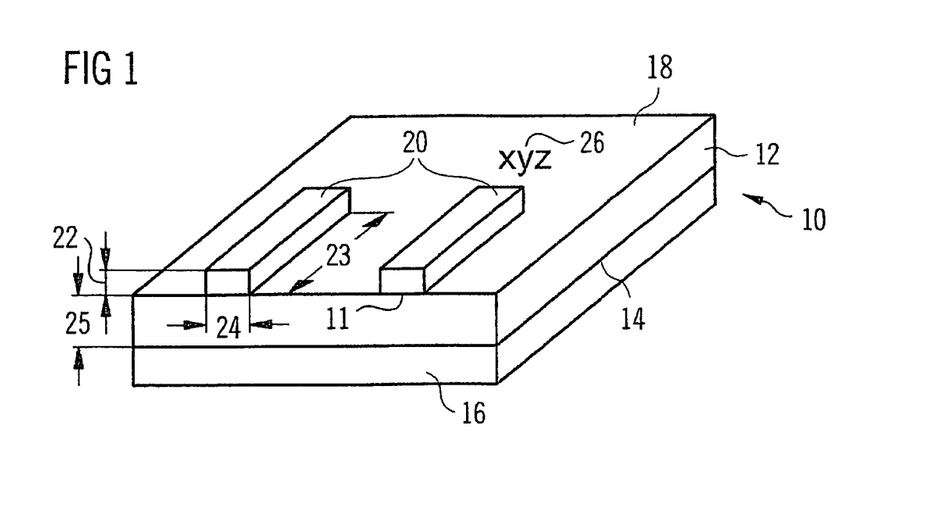
FIG. 1 shows a schematic illustration of a label according to one embodiment of the invention, in a perspective side view.

Referring to FIG. 1, a first embodiment of a label 10 according to the invention shown in a perspective side view is explained below. The label 10 comprises a flexible support layer 12. The support layer 12 can be produced from a multiplicity of materials. For example, it is conceivable for the support layer 12 to be made as a paper layer or plastic layer. In the context of the invention, it is likewise possible for the support layer 12 to be configured in a multi-layer structure, for example as a laminate.

An adhesive layer 16 is arranged on one face 14, for example an underside, of the flexible support layer 12. The adhesive layer 16 can partially or completely cover the face 14 of the flexible support layer 12. Several raised structural elements 20 are arranged on one face 18, for example a top face, of the flexible support layer 12. In this context, raised means that the structural elements 20 have a height 22 that considerably exceeds the thickness 25 of the support layer 12. The raised structural elements 20, therefore, do not merely constitute a slightly roughened surface of the support layer 12, as would be obtained, for example, by applying a printing ink to the label 10 or, for example, by applying Braille symbols to the label.

When the label 10 is applied to a container, for example a cylindrical ampoule for medicaments, the raised structural elements 20 are directed away from the container when the label 10 is secured to the container by means of the adhesive layer 16. The structural elements 20 can, for example, form abutment elements which engage in other abutment elements or simply bear on other abutment elements. The other abutment elements can, for example, be arranged on the inside wall of a hollow cylinder, for example of a syringe housing. When the container is inserted into the hollow cylinder, a mechanical form-fit is established between the structural elements of the label and the other structural elements. Consequently, a label is obtained which, by means of the raised structural elements 20, can perform a holding function between the container and the syringe housing.

The height 22 of the structural element can be greater than four times the support layer 12. If, for example, the support layer has a thickness of 100 μm, the structural element can have a height of more than 0.4 mm. A good holding function is achieved if the height of the structural elements is preferably between four times and twenty times the support layer. The structural elements can, for example, protrude from the surface of the support layer by a height of between 0.4 mm and 2 mm, particularly if the support layer has a height of 100 μm. It is thus possible to ensure with a high degree of probability that a medicament ampoule to which the label is secured will not be forced out of a housing of an injection device, for example of a syringe.

In FIG. 1, the raised structural elements 20 are indicated schematically with a rectangular cross section. However, it is also conceivable to design the raised structural elements 20 with another cross section, for example with a square or round cross section.

The structural elements can be block-shaped or cylinder-shaped projections, for example, protruding from the face 18 of the support layer 12. In the embodiment shown in FIG. 1, the structural elements 20 are applied to the support layer via a face that is delimited by the lengthwise sides 23 and breadthwise sides 24 of the structural elements. In order to permit a secure mechanical form-fit between the structural elements of the label and other structural elements, the structural elements applied to the support layer 12 of the label 10 can, for example, have a height that is at least twice as great as the shorter of the lengthwise and breadthwise sides 23, 24 (length and width) of the respective structural element 20.

The projections can, for example, be thickened at their end extending away from the support layer. In one possible embodiment, the structural elements can be mushroom-shaped, for example, with a thickening at the end directed away from the support layer. The thickening at that end of a structural element directed away from the support layer serves to engage in another structural element formed inversely with respect to the structural element of the label, such that a form-fit connection can be established between both structural elements.

The connection can be effected, for example, by a locking of one structural element in another structural element. Moreover, the structural element can be designed in such a way that the structural element arranged on the support layer of the label forms a bayonet catch with another structural element formed on another article. Thus, a form-fit and stable connection can be produced between the label, or the body on which the label is arranged, and the other article.

The raised structural elements 20 can be bevelled or rounded on the side faces. The structural elements preferably have sharp edges, by means of which it is possible to ensure engagement of one structural element in another structural element.

To be able to perform the abovementioned holding function, the raised structural elements 20 can be applied to the support layer 12 as a plastic web, for example. This can be done, for example, by adhesive bonding. However, it is also possible to design the raised structural elements 20 as a single-ply or multi-ply film layer. The shape of the raised structural elements 20 can be predefined by means of a stamping process, for example. The stamped-out contours of the film layer can be transferred to the support layer 12, for example by being adhesively bonded to the support layer 12.

In another embodiment, provision is made for the raised structural elements 20 to be printed on by means of a layer of paint. In order to produce the desired raised structural elements 20, it is possible, for example, to use a paint known as a printing ink for Braille. In contrast to Braille, the paint is applied to the support layer with a greater thickness than is the case when applying symbols in Braille. In contrast to Braille, the structural elements can be stamp-shaped projections that protrude from the support layer and at right angles to the surface of the support layer 12.

In addition, the label 10 can be provided, for example, with symbols 26 that represent information about the contents of a container, directions for use, or other information from the manufacturer. These symbols are usually printed onto the flexible support layer 12. As can be seen in FIG. 1, the letters "xyz" represent the symbols 26 on the label 10.

Figure 2:
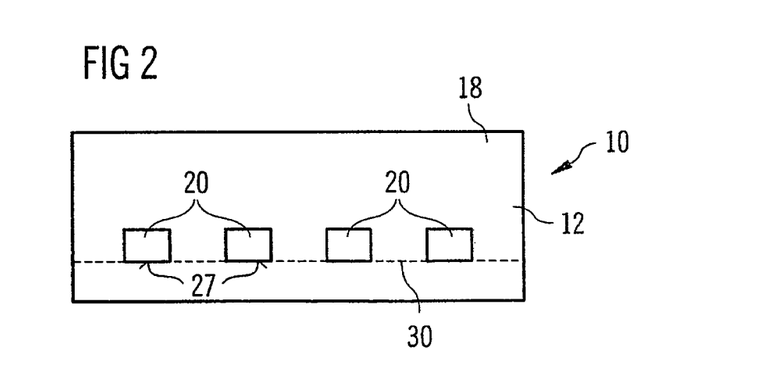
FIG. 2 shows a schematic illustration of a label according to another embodiment of the invention, in a plan view.

Referring to FIG. 2, another embodiment of a label 10 according to the invention shown in a plan view is described in greater detail below. The label 10 has a multiplicity of raised structural elements 20 which, as is shown in FIG. 1, are arranged on the top face 18 of the flexible support layer 12.

All of the structural elements 20 applied to the support layer 12 can have the same shape. The structural elements can be arranged on the support layer in such a way that a respective side face 27 of the structural elements in each case lies in one plane. These side faces 27 can form abutment surfaces of the structural elements 20 on which other structural elements bear with a form fit. According to the embodiment in FIG. 2, the structural elements 20 are arranged parallel to one another, for example. The parallel structural elements 20 each have a starting point arranged along a line 30. Consequently, a container provided with the label 10 can use the raised structural elements 20 as abutments, the contact surface of the abutment being defined along the line 30.

FIG. 2 also shows that the label 10 has a substantially rectangular profile. It is of course also possible to use other shapes for the label 10.

To be able to apply the label 10 to a container, however, it is advantageous that the label 10 has, along the line 30, an outer dimension which corresponds, for example, to an outer circumference of the container that is to be labelled. It is thus possible to ensure that no structural elements 20 overlap when the label 10 is applied.

Figure 3A:
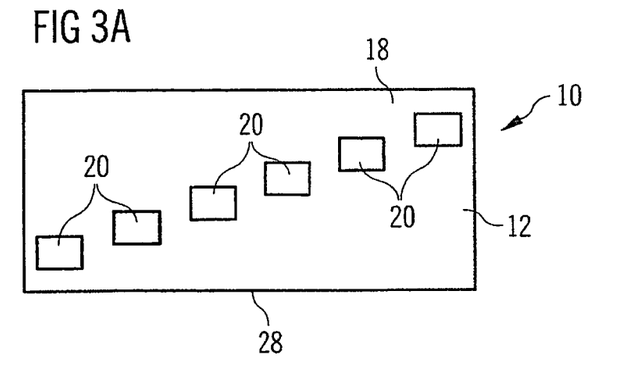
FIG. 3A shows a schematic illustration of a label according to another embodiment of the invention, in a plan view.

Referring to FIG. 3A, another embodiment of the label is disclosed below. The embodiment shown in FIG. 3A differs from the one shown in FIG. 2 in that a multiplicity of raised structural elements 20 are arranged in such a way that, when the label is applied to a cylindrical container, they supplement one another to form a thread on the outside of the container.

The illustrative embodiment shown in FIG. 3A thus represents a single winding of a thread. However, it is likewise conceivable to arrange several structural elements 20 such that several thread turns are formed. In the embodiment shown in FIG. 3A, the structural elements are designed as individual projections which are offset from one another at a short distance. The distance is chosen such that the projections form a thread turn.

Figure 3B:
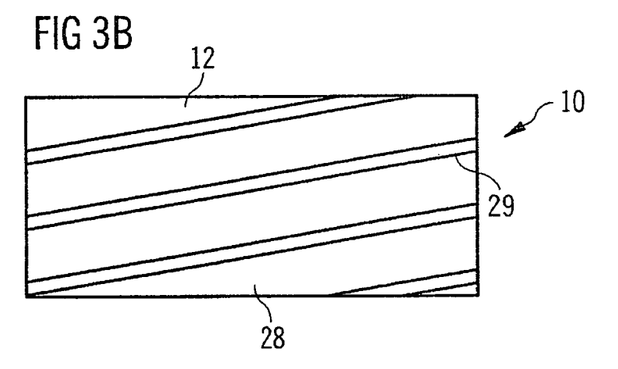
FIG. 3B shows a schematic illustration of a label according to another embodiment of the invention, in a plan view.

In the embodiment shown in FIG. 3B, web-shaped structural elements 29 are applied to the top face 18 of the support layer 12. Individual thread turns of the thread are obtained by several of the web-shaped structural elements 29 being arranged on the support layer and offset from one another at a short distance. The individual web-shaped structural elements 29 are arranged on the support layer obliquely with respect to the direction of the side edge 28 of the label. When the label is applied to a cylindrical container, the individual web-shaped structural elements form the thread.

Figure 3C:
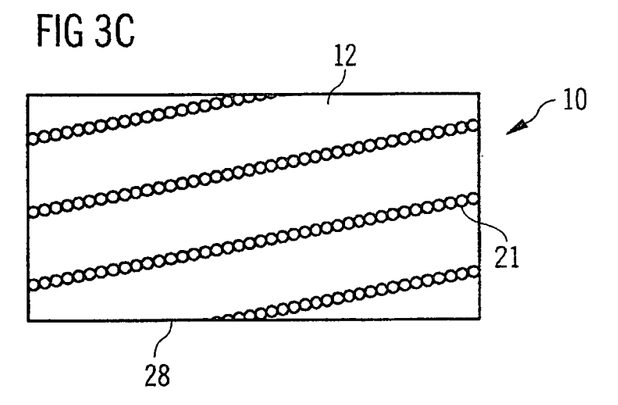
FIG. 3C shows a schematic illustration of a label according to another embodiment of the invention, in a plan view.

FIG. 3C shows an embodiment in which the structural elements are ball-shaped. A multiplicity of these ball-shaped structural elements 21 can be arranged such that the ball-shaped structural elements extend obliquely with respect to the direction of a side edge 28. Ball-shaped structural elements adjoining one another form a thread turn. The ball-shaped structural elements of the individual thread turns are arranged on the support layer and offset at a slight distance from each other. When the label is affixed to a cylindrical article, a thread is formed by the ball-shaped structural elements. The ball-shaped structural elements can be configured as balls made of a material chosen from glass or a plastic, for example a polymer. The balls 21 each have a diameter of less than 2 mm.

The structural elements of the embodiments shown in FIGS. 1, 2, 3A, 3B and 3C can be applied to the support layer 12 using an adhesive layer 11, for example. The adhesive can contain a material that hardens under the action of heat or radiation, for example by means of UV light.

In another embodiment, which is not shown in FIG. 2 or FIG. 3, the top face of the raised structural elements 20 can be provided with a structure such that the top faces of the structural elements 20 join together to form a thread. For this purpose, it is conceivable, for example, to provide the top face of the structural elements 20 with a structuring.

Figure 4:
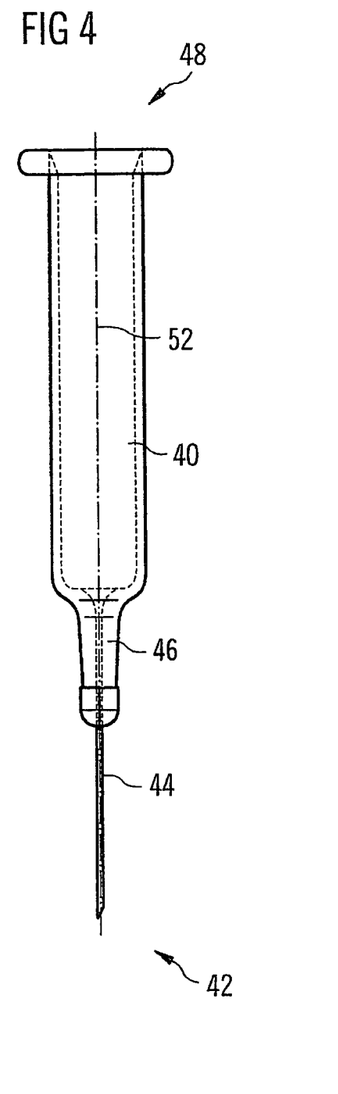
FIG. 4 shows a schematic illustration of a container according to one embodiment of the invention, in a cross-sectional view.

The use of the raised structural elements 20 on the label 10 is explained in more detail below. Referring to FIG. 4, a cylindrical container 40 is shown on which the label 10 can be arranged. The container 40 is, for example, a cartridge for a medical injection device, for example an injection pen or the like. For this purpose, the container 40, at its distal end 42, has a needle 44.

The needle 44 is joined to the container 40 via a flange designed as a needle holder. A finger flange 50, for example, is located at the proximal end 48 of the container 40. The container 40 is substantially cylindrical, the cylinder axis 52 being indicated by a broken line in FIG. 4. The finger flange 50 usually extends radially, that is to say perpendicular to the cylinder axis 52.

Figure 5:
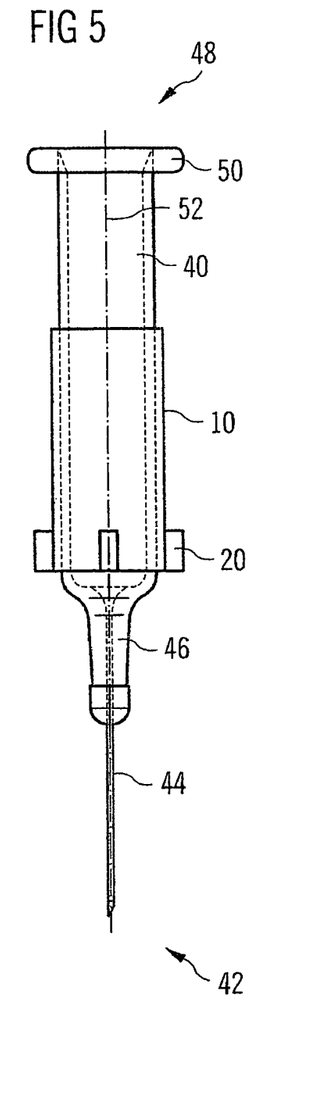
FIG. 5 shows a schematic illustration of a container with a label according to one embodiment of the invention, in a cross-sectional view.

Referring to FIG. 5, the container 40 is shown after it has been provided with the label 10 in an embodiment according to FIG. 2. The raised structural elements 20, which are arranged at the end of the label 10 directed towards the distal end 42 of the container 40, point radially outwards. The structural elements 20 are thus directed away from the container 40.

As can be seen in FIG. 5, a container 40, which is provided with the label 10 according to the invention, not only has the finger flange and the needle holder 46, but also the structural elements 20 which can be used as abutments for securing the container 40 in a housing. However, it goes without saying that the invention is not limited to the use shown in FIG. 5. For example, the label 10 can also be used on a container 40 that has no finger flange.

In brief, the holding function performed by the raised structural elements 20 alone, or in combination with other holding points, affords a simple way of securing a container 40 inside a housing. The label 10 can either give support to holders that are already present or, alternatively, it can be provided as the sole holding means.

Figure 6:
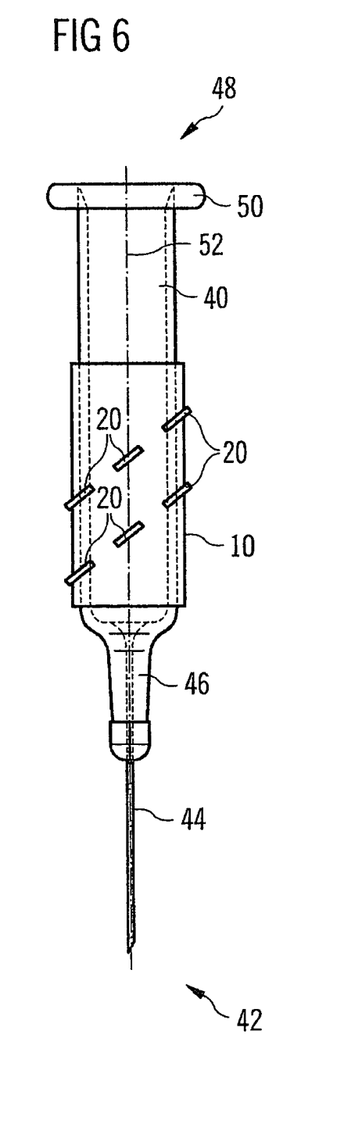
FIG. 6 shows another schematic illustration of a container with a label according to one embodiment of the invention, in a cross-sectional view.

Referring to FIG. 6, a container 40 is now described which is provided with a label 10 similar to the embodiment according to FIG. 3. In contrast to the embodiment shown in FIG. 5, the raised structural elements 20 in this case form a thread on the outside of the container 40. Consequently, the container 40 can be positioned or secured in a housing for example. For this purpose, corresponding perforations would have to be formed on the housing and form an inner thread.

Figure 7:
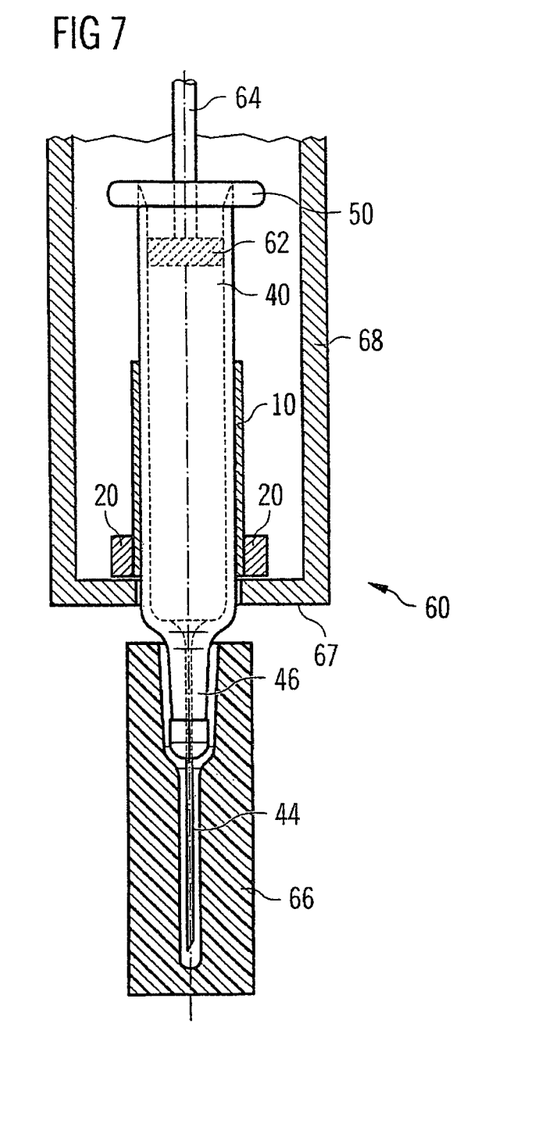
FIG. 7 shows a schematic illustration of a medical injection device according to one embodiment of the invention, in a cross-sectional view.

Referring to FIG. 7, a medical injection device is now described which makes use of the invention. The injection device 60 is, for example, an injection pen, which is normally used for self-medication. However, it is also conceivable that the medical injection device 60 is a syringe for other applications. The injection device 60 comprises the container 40 in the form of a medicament cartridge.

In addition to the features already explained with reference to FIGS. 4 to 6, a piston 62 and a piston rod 64 are shown in FIG. 7 and serve to administer the medicament contained in the container 40. As is generally known in the art, the piston rod 64 can be provided with a suitable mechanism for administering a dose. Since the mechanism for administering a dose is not part of the subject matter of the invention, it will not be explained in any more detail below.

Medical injection devices 60 which are provided at their distal end with a needle are normally protected by a needle guard device 66 against accidental contact. As can be seen from FIG. 7, the needle guard device 66 can reach as far as the shoulder formed between the outer walls of the container and the needle holder 46. To be able to secure the container 40 safely in the housing 68, an abutment in the form of the raised structural elements 20 is provided on the label 10. Consequently, when the piston 62 is pushed forwards via the piston rod 64, the container 4 cannot slip out of the housing 68, because the raised structural element 20 establishes a form-fit connection with another structural element 67 of the housing 68.

As has already been explained in connection with FIG. 5, a finger flange can help secure the container 40 on the housing 68. However, the label 10 can also be used on containers that have no finger flange. It would also be conceivable for the finger flange to be replaced by another label 10 (not shown in FIG. 7). In brief, the invention allows a medical container, for example, to be retained in a housing by means of a form fit.

Particularly when a needle guard device is used, it can happen that the diameter of the latter is greater than the diameter of the container 40. As a result, the shoulder lying at the transition between container and needle can no longer be used as an abutment. The sole use of the finger flange would increase the tolerances during production of an injection pen. In the worst case, a situation could arise in which, when the injection pen is actuated, the entire syringe is forced out of the housing, for example on account of material weakness.

This is avoided according to the invention, and positioning and/or fixing is achieved by means of a defined abutment or a thread. Since medical containers are usually provided with a label for identification of their contents, the invention does not add to the complexity of producing an injection pen.

The invention is not limited by the description on the basis of the illustrative embodiments. Instead, the invention encompasses every novel feature and also every combination of features, which in particular includes every combination of features in the patent claims, even if said feature or said combination is not itself explicitly mentioned in the patent claims or in the illustrative embodiments.

Although only a few embodiments of the present invention have been shown and described, it is to be understood that many changes and modifications may be made thereunto without departing from the spirit and scope of the invention.

The invention claimed is:

1. Label (10) for labelling a container (40), comprising a flexible support layer (12) which, on one face (18), is provided at least partially with at least one raised structural element (20), wherein the structural element (20) is designed in such a way that, when the label is applied to the container (40), the structural element (20) is directed away from the container (40), and wherein the structural element (20) is formed as an abutment element which is able to engage in another structural element formed on a device to establish a form-fit connection with the other structural element (67) so that the structural element (20) is able to perform a holding function between the container (40) and the device.

2. Label according to claim 1, in which the structural element (20) has a height (22) that is greater than four times the support layer (12).

3. Label according to claim 1, in which the structural element (20) has a height (22) that is greater than 0.4 mm.

4. Label according to claim 1,
in which the structural element (20) is applied to the support layer (12) via a structural element face that is delimited by sides (23, 24) of the structural element,
wherein the structural element (20) has a height (22) that is at least twice as great as the shorter of the sides (23, 24) of the structural element face.

5. Label according to claim 1, in which a multiplicity of structural elements (20) are applied to the face (18) of the support layer (12), and, when the label is applied to the container (40), this results in a multiplicity of holding elements directed away from the container (40).

6. Label according to claim 5, in which the multiplicity of structural elements (20) are formed from a multiplicity of ball-shaped elements (21), wherein the ball-shaped elements are arranged on the face (18) of the support layer (12) in such a way that, when the label is applied to the container, the ball-shaped elements (21) form the thread.

7. Label according to claim 5,
in which each of the structural elements (20) of the multiplicity of structural elements has a side face (27),
wherein the structural elements (20) are arranged on the support layer (12) in such a way that the respective side face (27) of the structural elements is arranged in one plane.

8. Label according to claim 1, in which the structural element is bonded to the support layer (12) by means of an adhesive layer (11).

9. Label according to claim 1, in which the structural element (20) is applied as a plastic web (29) to the support layer.

10. Label according to claim 9, in which the plastic web (29) is adhesively bonded to the support layer (12).

11. Label according to claim 1, in which the structural element (20) is applied as a structured color layer to the support layer.

12. Label according to claim 11, in which the structured color layer is printed onto the support layer by means of a paint.

13. Label according to claim 12, in which the paint corresponds to a printing ink for Braille.

14. Label according to claim 1, in which the structural element (20) is applied as a structured film layer to the support layer (12).

15. Label according to claim 14, in which the structured film layer (20) is affixed to the support layer (12).

16. Label according to claim 1, in which the flexible support layer (12) additionally comprises symbols that represent information about the contents of the container (40), directions for use, or instructions from the manufacturer.

17. Label according to claim 16, in which the symbols are printed onto the flexible support layer (12).

18. Label according to claim 1, which label can be secured to the container (40) by means of an adhesive layer (16) applied to another face (14) lying opposite the face (18) of the support layer (12).

19. Label according to claim 1, in which, when the label is applied to the container (40), the structural element (20) is suitable as an abutment for securing the container (40) in a housing (68).

20. Label according to claim 1, in which several structural elements (20) are applied parallel to one another on the support layer (12).

21. Label according to claim 20, in which the parallel structural elements (20) each have a starting point, and these starting points are arranged along a line (30).

22. Label according to claim 1, in which the container (40) is cylindrical, and the structural element (20) is arranged along an axial direction (52) of the container.

23. Label according to claim 1, in which the structural element (20) forms a thread when the label is applied to the container (40).

24. Label according to claim 23, in which, when the label is applied to the container, gaps in the structural element (20) form the thread.

25. Label according to claim 1, in which an outer dimension of the label (10) corresponds to an outer circumference of the container (40).

26. Medical injection device, comprising:
a label (10) with a flexible support layer (12) which, on one face (18), is provided at least partially with at least one raised structural element (20),
a cylindrical container (40) which receives a medical product and which is provided with the label (10), wherein the structural element (20) forms a projection directed away from the container (40), and
a housing (68) in which the container (40) is arranged, the housing having another structural element (67), wherein the structural element (20) is formed as an abutment element which is able to engage in the other structural element (67) to establish a form-fit connection with the other structural element (67) so that the structural element (20) is able to perform a holding function between the container (40) and the housing (68).

27. Medical injection device according to claim 26, in which the label is arranged on the container via a face (16) lying opposite the face (18).

28. Medical injection device according to claim 26, in which the structural element (20) has a height (22) that is greater than four times the support layer (12).

29. Medical injection device according to claim 28, in which the structural element (20) has a height (22) that is greater than 0.4 mm.

30. Medical injection device according to claim 26,
in which the structural element (20) is applied to the support layer (12) via a structural element face that is delimited by sides (23, 24) of the structural element,
wherein the structural element (20) has a height (22) that is at least twice as great as the shorter of the sides (23, 24) of the structural element face.

31. Medical injection device according to claim 26, in which a multiplicity of structural elements (20) are applied to the face (18) of the support layer (12), and, when the label is applied to the container (40), this results in a multiplicity of holding elements directed away from the container (40).

32. Medical injection device according to claim 26, in which the structural element is bonded to the support layer (12) by means of an adhesive layer (11).

33. Medical injection device according to claim 26, in which the cylindrical container (40) is a medicament ampoule or medicament cartridge.

34. Medical injection device according to claim 26, in which the housing (68) is part of an injection pen or of a syringe.

35. Medical injection device according to claim 26, in which the container (40), at a distal end, has a needle (44) which is surrounded by a needle guard device (66).

36. Method for producing a label, comprising the following steps:
providing a flexible support layer (12), and
applying at least one raised structural element (20) to one face (18) of the support layer (12),
wherein the structural element (20) is designed in such a way that, when the label is applied to a container (40), the structural element (20) is directed away from the container (40), and wherein the structural element (20) is formed as an abutment element which is able to engage in another structural element formed on a device to establish a form-fit connection with the other structural element (67) so that the structural element (20) is able to perform a holding function between the container (40) and the device.

37. Method according to claim 36, in which the structural element (20) is applied to the support layer (12) with a height (22) that is greater than four times the support layer (12).

38. Method according to claim 36, in which the structural element (20) is applied to the support layer (12) with a height (22) that is greater than 0.4 mm.

39. Method according to claim 36,
in which the structural element (20) is applied to the support layer (12) via a structural element face that is delimited by sides (23, 24) of the structural element,
wherein the structural element (20) is applied to the support layer (12) with a height (22) that is at least twice as great as the shorter of the sides (23, 24) of the structural element face.

40. Method according to claim 36, in which the structural element is bonded to the support layer (12) by means of an adhesive layer (11).

* * * * *